United States Patent [19]
Pope

[11] 4,146,023
[45] Mar. 27, 1979

[54] INTRAUTERINE CONTRACEPTIVE DEVICE

[76] Inventor: Maurice R. Pope, 87 Sander Rd., New Germany, Natal, 3600, South Africa

[21] Appl. No.: 837,089

[22] Filed: Sep. 28, 1977

[30] Foreign Application Priority Data

Sep. 28, 1976 [ZA] South Africa .................. 76/5798

[51] Int. Cl.² ......................................... A61F 5/46
[52] U.S. Cl. ................................................ 128/130
[58] Field of Search ........................ 128/127–131, 128/260

[56] References Cited

U.S. PATENT DOCUMENTS

| | | | |
|---|---|---|---|
| 3,397,691 | 8/1968 | Majzlin | 128/130 |
| 3,820,535 | 6/1974 | Marco | 128/130 |
| 4,005,707 | 2/1977 | Moulding | 128/130 |
| 4,054,131 | 10/1977 | Kessel | 128/130 |

Primary Examiner—Lawrence W. Trapp
Attorney, Agent, or Firm—Young & Thompson

[57] ABSTRACT

An intrauterine contraceptive device of the type comprising the figure 7, the invention comprising the provision of a downwardly-extending element to the end of horizontal portion of the 7, the downwardly-extending element having a thread anchored thereto, the thread passing slidably through an orifice at the bottom end of the vertical portion of the 7.

2 Claims, 3 Drawing Figures

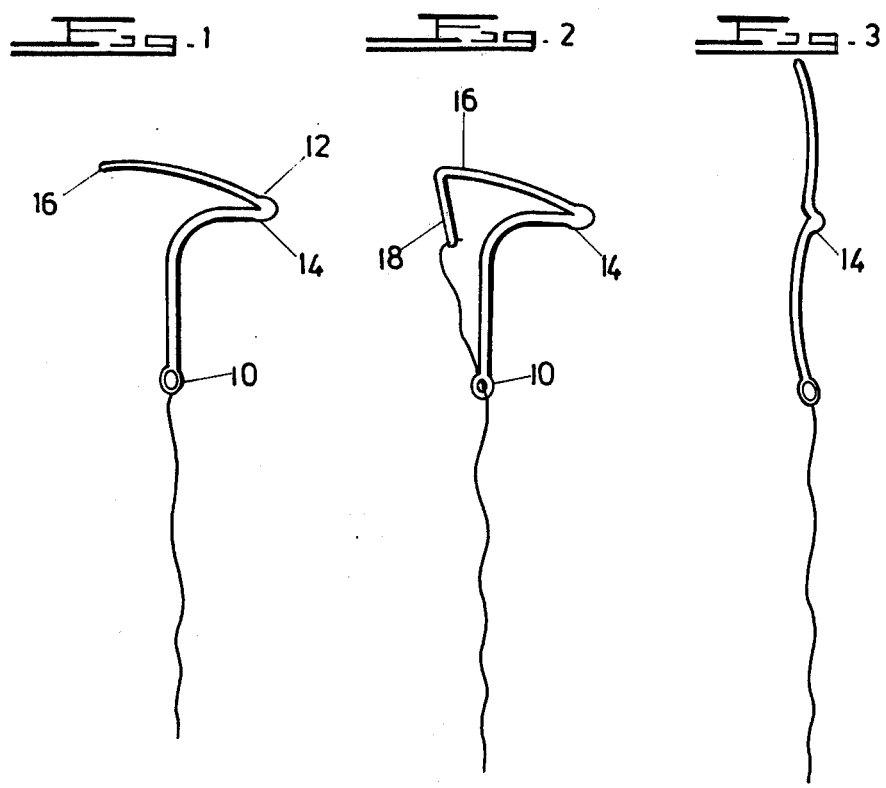

INTRAUTERINE CONTRACEPTIVE DEVICE

This invention relates to intrauterine contraceptive devices, and in particular to a device of the type marketed as GRAVIGARD (registered trade mark of G. D. Searle & Company).

Devices of that type are substantially in the form of the figure 7 moulded from plastics material. Additional plastic is added in the form of a bulb at the angle of the 7 and the lower end is thickened to accommodate a hole for the removal thread.

Insertion of the device is accomplished by squeezing the 7 together and inserting the squeezed-together ends into a plastic straw until only the bulb protrudes. Upon insertion the device is ejected by means of a plunger and it reassumes the figure 7 due to the rigidity and elasticity of the plastic material.

Withdrawal is accomplished by drawing the thread. The horizontal portion of the 7 is bent upwardly to a degree limited by the strength of the bulb at the angle and the device is then drawn through the cervical canal. As this canal is of the order of 4 mm the withdrawal causes pain and discomfort. Another disadvantage of this type of device is that the necessary rigidity of the plastic used results in a resistance of the device towards uterine contractions and there is a tendency for the open end of the horizontal portion to perforate the uterine wall and for the device to migrate out of the uterus.

It is an object of the present invention to overcome or at least minimise these disadvantages.

According to the invention a IUCD includes a moulding in the form of a figure 7, the end of the horizontal portion having a downwardly-extending element, and the bottom end of the vertical portion having an orifice adapted slidably to accommodate a thread which is anchored to the lower end of the downwardly-extending element.

In a preferred form of the invention the downwardly-extending element is of the order of one centimeter in length and is at an angle to the horizontal portion of the 7 so that it follows the contour of the wall of the uterus.

It will be appreciated that withdrawal of the device is effected by drawing the various portions of the device together, thus offering the least possible resistance and therefore pain and discomfort to the patient.

Furthermore the downwardly-directed element prevents perforation of the uterine wall, previously caused by the free end of the horizontal portion of the 7.

The arrangement also allows for a more flexible plastic material or construction to be used as the downwardly extending element exerts pressure against the vertical portion of the 7 and aids in returning the device to its configuration after insertion.

The invention will become clearer to the reader of this specification by reference to the accompanying drawings, in which:

FIG. 1 is a side view of the conventional IUCD 7 device,

FIG. 2 is a similar view of one example of the present invention, and

FIG. 3 is a similar view of the position assumed by the conventional device when being withdrawn.

In FIG. 1 the end 10 is provided with an orifice for receiving the end of a thread. The angle 12 is enlarged by means of the bulb 14 and the end 16 of the horizontal portion is free. As explained above, the end 16 can be responsible for perforation of the uterine wall. When removing the device the thread is pulled and the device assumes the position shown in FIG. 3 and by virtue of the rigidity of the device, substantial pain and discomfort are caused, particularly by the bulb 14.

The device shown in FIG. 2 has a downwardly-extending element 18 which substantially follows the shape of the uterine wall. A thread attached to the end of this element passes through an orifice at 10 and when pulled the device is folded up and passes easily through the cervical canal with greatly reduced pain and discomfort.

The thread may be attached to the end of the element by being tied around a narrowed portion. Alternatively a suitable hole may be formed.

To improve retention a spike may be added to the bulb 14.

I claim:

1. An intrauterine contraceptive device comprising a moulding in the form of the number 7, the end of the horizontal portion of which has a downwardly-depending element, the bottom end of the vertical portion having an orifice adapted slidably to accommodate a thread which is anchored to the lower end of the downwardly-extending element.

2. The device of claim 1 in which the downwardly-extending element is at an angle to the horizontal portion of the 7 so that it follows the contour of the wall of the uterus.

* * * * *